US00PP09613P

United States Patent [19]

Meilland

[11] Patent Number: Plant 9,613

[45] Date of Patent: Jul. 30, 1996

[54] FLORIBUNDA ROSE PLANT NAMED 'MEISOCRAT'

[75] Inventor: Alain A. Meilland, Antibes, France

[73] Assignee: The Conard-Pyle Company, West Grove, Pa.

[21] Appl. No.: 492,134

[22] Filed: Jun. 19, 1995

[51] Int. Cl.[6] ..... A01H 5/00

[52] U.S. Cl. ..... Plt./26

[58] Field of Search ..... Plt./22, 26, 25, Plt./27

*Primary Examiner*—Howard J. Locker

*Attorney, Agent, or Firm*—Burns, Doane, Swecker & Mathis, L.L.P.

[57] ABSTRACT

A new and distinct variety of Floribunda rose plant is provided which abundantly forms attractive light Carmine Pink blossoms possessing a large number of petals and having a configuration similar to that of an old-fashioned rose. The blossoms exhibit a distinctive fragrance that is reminiscent of green apple. The plant exhibits a compact and bushy growth habit. Attractive dark green and glossy vegetation is formed. The new variety is particularly well suited for growing as ornamentation in the landscape.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) was the product of the cross of the 'Meituraphar' variety (non-patented in the United States) and the 'Mrs. John Laing' variety (non-patented in the United States). The male parent (i.e., the pollen parent) of the new variety was the 'Egeskov' variety (non-patented in the United States). The parentage of the new variety can be summarized as follows:

('Meituraphar'×'Mrs. John Laing')×'Egeskov'.

The seeds resulting from the above pollination were sown and 371 small plants were obtained which were physically and biologically different from each other. Selective study resulted in the identification of a single plant of the new variety.

It was found that the new variety of Floribunda rose plant of the present invention possesses the following combination of characteristics:

(a) forms in abundance attractive light Carmine Pink blossoms possessing a large number of petals and having a configuration similar to that of an old-fashioned rose,
(b) exhibits a compact and bushy growth habit,
(c) exhibits a fragrance,
(d) forms attractive dark green and glossy vegetation, and
(e) is particularly well suited for growing as ornamentation in the landscape.

The new variety has undergone asexual propagation by a number of routes in France, including budding grafting, and cuttage. The characteristics of the new variety have been found to be strictly transmissible by such asexual propagation from one generation to another in both France.

The new variety has been named the 'Meisocrat' variety.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were two years of age and were observed during September while budded on *Rosa froebelii* understock and growing outdoors at Le Cannet des Maures, Var. France. A truer blossom coloration than illustrated in the photograph is presented hereafter with reference to the R.H.S. colour Chart. More specifically, the blossoms are Carmine Pink and possess less orange coloration than illustrated in the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates specimens of two leaves with three leaflets—upper surface (below) and under surface (above);

FIG. 15—illustrates specimens of two leaves with five leaflets—upper surface (left) and under surface (right); and FIG. 16—illustrates specimens of two leaves with seven leaflets—upper surface (left) and under surface (right).

DETAILED DESCRIPTION

Figures 1, 2, 3, 4, 5, 6, 7, 8, 9, 10, 11, 12, 13, 14, 15, 16:
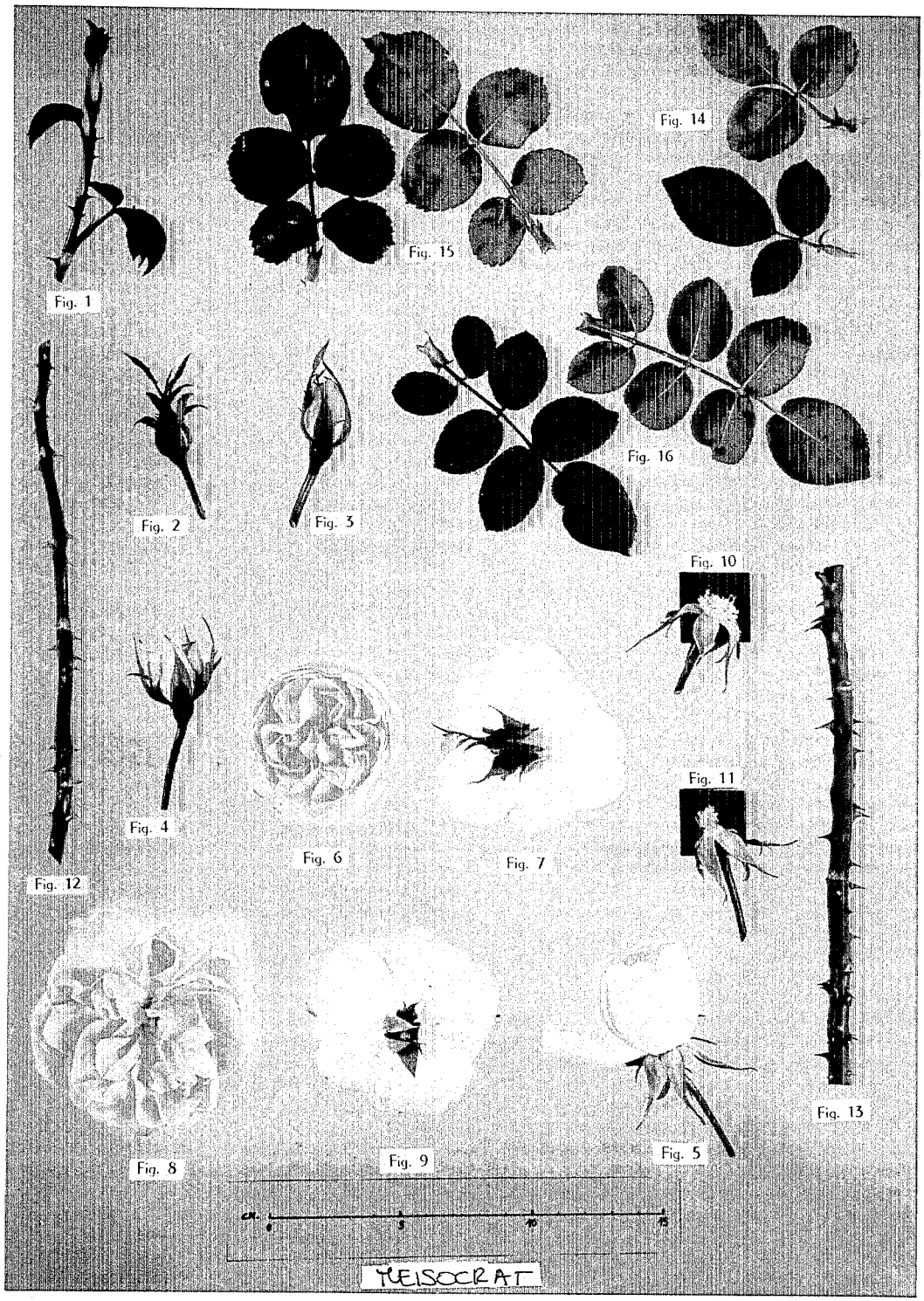

The chart used in the identification of the colors is that of the Royal Horticultural Society (R.H.S. Colour Chart). The terminology which precedes reference to the chart has been added to indicate the corresponding color in more common terms. the desciption is based on two year old specimens of the new variety during September while budded on *Rosa froebelii* understock and growing outdoors at Le Cannet des Maures, Var, France.

Class: Floribunda.

Plant:

*Height.*—Plants commonly achieve a height of approximately 70 to 90 cm. at the end of the growing season. In view of the Floribunda classification floral stem lengths typically are not measured; however, such stem lengths commonly are believed to be less than about 45 cm.

*Habit.*—Bushy.

Branches:

*Color.*—Young stems: light green, Green Group 143C and tinged with reddish coloration. Adult wood: medium green, Green Group 137D.

*Thorns.*—Size: medium. Quantity: average. Color: greenish on young stems, and reddish on mature wood.

Leaves:

*Stipules.*—Adnate, pectinate, very large and linear.

*Petioles.*—Upper surface: striped reddish on young foliage and medium green on adult foliage with more or less glandular edges. Under surface: rarely exhibit small prickles.

*Leaflets.*—Number: 3, 5, and 7. Shape: oval. Serration: single and regular. Texture: coriaceous. General appearance: dense, glossy, dark green, and very ornamental. Color (young foliage): upper surface: light green, Green Group 143A, and more or less edged and suffused with reddish coloration. under surface: light green, Yellow-Green Group 144A and widely suffused with reddish coloration. Color (adult foliage): upper surface: medium green, Green Group 137A. under surface: light green, Green Group 137D.

Inflorescence:

*Number of flowers.*—Commonly approximately 6 to 15 flowers per stem. The flower productivity is good and generally corresponds to that of a better flowering Floribunda variety.

Peduncle.—Light green with some reddish coloration, more or less glandular with some small prickles or hairs, and approximately 5 to 6 cm. in length on average.

*Sepals.*—Upper surface: tomentose, greenish with foliar extensions, and widely tinged with reddish coloration. Under surface: light green and more or less tinged with reddish coloration, and commonly possess extensions.

*Buds.*—Shape: globular. Length: approximately 2.5 to 3 cm. on average. Size: large. Color upon opening: upper surface: Carmine Pink, Red Group 52C at the margins, light Carmine Pink, Red Group 52D at the middle, and Empire Yellow, Yellow Group 11D at the base, with the external petals being somewhat lighter. under surface: Carmine Pink, Red Group 52C and suffused with light Carmine Pink, Red Group 52D at the middle.

Flower.—Shape: cup-shaped in the middle and somewhat flat at the perimeter. Diameter: approximately 7 to 8 cm. on average. Color (when opening begins): upper surface: Carmine Pink, Red Group 52C at the margins, light Carmine Pink, Red Group 52D at the middle, and Empire Yellow, Yellow Group 11D at the base, with the external petals being somewhat lighter. under surface: Carmine Pink, Red Group 52C and suffused with light Carmine Pink, Red Group 52D at the middle. Color (when blooming): upper surface: Carmine Pink, Red Group 52C at the margins, light Carmine Pink, Red Group 52D at the middle, and Empire Yellow, Yellow Group 11D at the base, with the external petals being somewhat lighter. under surface: Carmine Pink, Red Group 52C and suffused with light Carmine Pink, Red Group 52D at the middle. Color (at end of opening): upper surface: Carmine Pink, Red Group 52C at the margins, light Carmine Pink, Red Group 52D at the middle, and Empire Yellow, Yellow Group 11D at the base, with the external petals being somewhat lighter. under surface: Carmine Pink, Red Group 52C and suffused with light Carmine Pink, Red Group 52D at the middle. Fragrance: medium, and reminiscent of green apple. Lasting quality: long. The blossoms commonly last 8 days or more on the plant and a lesser number of days when cut and placed in a vase. The lives of such blossoms are greatly influenced by the season of the year and the environmental conditions that are encountered. Petal drop: good with the petals becoming cleanly detached when fully mature. Petal form: rounded. Petal number: approximately 90 to 100 on average. Stamen number: approximately 15 to 20 on average. Anthers: ochre in coloration. Filaments: yellowish in coloration. Pistils: approximately 40 to 50 on average. Stigmas: ochre. Styles: greenish in coloration with a fuchsine tip. Receptacle: medium green, smooth, and in longiudinal section in the shape of a pitcher. Hips: round-shaped hips commonly are formed.

Development:

*Vegetation.*—Strong.

*Blooming.*—Abundant.

*Resistance to diseases.*—Good.

*Aptitude to be forced.*—Good with a slight sensitivity to Marssonina.

I claim:

1. A new and distinct variety of Floribunda rose plant characterized by the following combination of characteristics:

(a) forms in abundance attractive light Carmine Pink blossoms possessing a large number of petals and having a configuration similar to that of an old-fashioned rose,
(b) exhibits a compact and bushy growth habit,
(c) exhibits a fragrance,
(d) forms attractive dark green and glossy vegetation, and
(e) is particularly well suited for growing as ornamentation in the landscape;

substantially as herein shown and described.

* * * * *

CM.
0
5
10
15
MEISOCRAT